United States Patent [19]

Venero et al.

[11] Patent Number: 5,051,510

[45] Date of Patent: Sep. 24, 1991

[54] PIPERIDINE DERIVATIVES AS ANTIHISTAMINICS

[75] Inventors: Aurelio O. Venero; Antonio T. Avello, both of Vizcaya, Spain

[73] Assignee: Fabrica Espanola de Productos Quimicos y Farmeceuti-Cos S.A. (FAES), Vizcaya, Spain

[21] Appl. No.: 486,097

[22] Filed: Feb. 28, 1990

[30] Foreign Application Priority Data

Feb. 28, 1989 [EP] European Pat. Off. ........ 89500022.2

[51] Int. Cl.$^5$ ........................................... C07D 401/12
[52] U.S. Cl. ...................................... 546/200; 546/198
[58] Field of Search .................. 546/15, 198, 200, 208, 546/217, 223, 233, 234

[56] References Cited

U.S. PATENT DOCUMENTS 4,621,097 11/1986 Butler et al. ...................... 514/421

Primary Examiner—Mary C. Lee
Assistant Examiner—Jacqueline Haley
Attorney, Agent, or Firm—Wenderoth, Lind & Ponack

[57] ABSTRACT

New antihistaminic piperidine derivatives of general structural formula I are prepared by reacting 4-piperidinealkylamines with carboxylic acids or their active derivatives, such as lower-alkyl esters or the acid chlorides.

The obtained new piperidine carboxamide compounds show potent antihistaminic activity as specific antagonists of histamine H1-receptors.

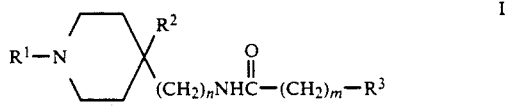

8 Claims, No Drawings

PIPERIDINE DERIVATIVES AS ANTIHISTAMINICS

INTRODUCTION

The search for new antihistaminic compounds is centered on the synthesis of pure H1 antagonists having a greater affinity for peripheral rather than central histamine receptors, this property being increased as drug ability to cross the hematoencephalic barrier diminishes, and small, if any, antagonism towards other biological significant amines.

Some 4-piperidinealkylamine derivatives have been reported to have a marked activity as specific antagonists of the histamine H1-receptors (Eur. Pat. Appl. No. 8850050.5).

The present invention relates to the preparation of new 4-piperidinealkylamine derivatives useful as antihistamines and in the treatment of allergies.

It consists in reacting an active derivative of a carboxylic acid, or the carboxylic acid itself, with a piperidinealkylamine to form a carboxamide of general structural formula I, as well as the physiologically acceptable salts thereof.

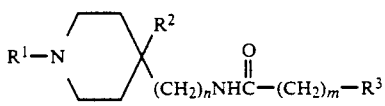

In which the substituent R1 may represent:

A lower-alkyl radical containing up to 4 carbon atoms such as methyl, ethyl, 1-methyl-ethyl or butyl;

An aryl-alkylene grouping AR—CH2 or AR—CH2—CH2, in which AR may have the following meanings:

phenyl or a phenyl radical substituted by from 1 to 2 of the following substituents: F, Cl, Br, I, CH3, C2H5, OH, OCH3, OCOCH3, CF3, NH2, NHCOCH3, NHSO2CH3, NO2 and COOH;

In which n=0, 1, 2;

In which m=0, 1, 2;

In which the substituent R2 is: H, OH;

In which the substituent R3 represents the following radicals:

1H-2-isoindolyl-1,3(2H)-dioxo, 1-(1H-2-isoindolyl-1,3(2H)-dioxo)-ethyl, 1H-2-isoindolyl-1,3(2H)-dioxo-4,4a, 5,6,7,7a-hexahydro, 1H-2-isoindolyl-1,3(2H)-dioxo-4,4a, 7,7a-tetrahydro, 1H-2-isoindolyl-1,3(2H)-dioxo-4-nitro, 1H-2-isoindolyl-1,3(2H)-dioxo-4-amino, 1H-pyrrolyl-2,5-dihydro-2,5-dioxo, 1-pyrrolidinyl-2,5-dioxo, 8-azaspiro<4,5>decan-8-yl-7,9-dioxo, 1,2-benzoisothiazol-2-yl-6-carboxy-3(2H)oxo 1,1-dioxide, 1,2-benzoisothiazol-2-yl-3(2H)oxo 1,1-dioxide, 1,2-benzoisothiazol-2-yl-6-nitro-3(2H)oxo 1,1-dioxide, 1,2-benzoisothiazol-2-yl-6-amino-3(2H)oxo 1,1-dioxide, 1,2-benzoisothiazol-2-yl-6-acetylamino-3(2H)oxo 1,1-dioxide, 1,2-benzoisothiazol-2-yl-6-(methylsulfonylamino)-3(2H)oxo 1,1-dioxide, phenoxy, 4-methylphenoxy, 4-chlorophenoxy, 4-fluorophenoxy, 4-chloro-2-methylphenoxy, 4-acetoxyphenoxy, 3-acetoxyphenoxy, 4-hydroxyphenoxy, 3-hydroxyphenoxy, 4-aminophenoxy, 3-aminophenoxy, 4-nitrophenoxy, 3-nitrophenoxy, 4-methoxyphenoxy, 3-methoxyphenoxy, amino, acetylamino, methylsulfonylamino, 1-aminoethyl, 1-acetylamino-ethyl and 1-(methylsulfonylamino)-ethyl.

As examples of said pharmocologically acceptable salts, there may be employed the hydrochloride, hydrobromide, maleate, tartrate, citrate and ethanedioate salts of said compound of formula I.

The 4-piperidinealkylamines employed to perform this invention are represented by the general formula II:

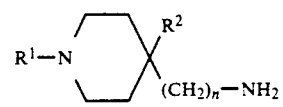

Most of these piperidinamines are sufficiently known compounds, described in the literature. Some of them have not been reported but may be prepared in good yields by well established procedures. So, N-substituted 4-piperidinealkylamines other than N-phenylmethyl and N-2-phenylethyl are prepared starting from the corresponding primary amines and diethyl acrylate to give N-substituted-4-piperidinones (Elpern, B. et al., J. Am. Chem. Soc. 80, 4916 (1958)). These later compounds are transformed into the desired amines of formula II by reductive methods (R2=H, n=0: Harper, N. H. et al., J. Med. Chem. 7, 729 (1964)) or by condensation with nitromethane and then reduction to the amine (R2=OH, n=1; Regnier, G. Chim. Ther. 3, 185 (1969)). The reduction of 4-piperidinones with NaBH4 and subsequent treatment of the obtained piperidinols with KCN yields 4-cyanopiperidines which are reduced to compounds of formula II (R2=H, n=1) with LiAl H4.

The Wittig-Horner reaction of the 4-piperidinones leads to 4-piperidinethanamines II (R2=H, n=2).

As regards the carboxylic acids employed, and their active derivatives, these are easily available products according to the literature data.

The invention is performed by reacting carboxylic acids of structural formula R3-(CH2)m-COOH, with a piperidineamine II, to afford compounds of general structural formula I.

It is advantageous to use an active derivative of the carboxylic acid, such as the acid chloride R3-(CH2)m-COCl, or a lower-alkyl ester R3-(CH2)m-COOR4 (R4=methyl, ethyl, 2-methoxy-ethyl), the process remaining essentially the same.

The examples below illustrate the preparation of compounds of formula I and as such are not to be considered as limiting the invention.

EXAMPLES

Example 1

1,3(2H)-dioxo-N-<1-(2-phenylethyl)-4-piperidinyl>-1H-2-isoindoleacetamide, hydrochloride A solution of 83 g of 1,3(2H)-dioxo-1H-2-isoindoleacetic acid chloride in 500 ml of dry tetrahydrofurane is dropwise added, with stirring and external cooling, to a solution of 65 g of 1-(2-phenylethyl)-4-piperidinamine in 1500 ml of dry THF. The white solid is collected after 2 h at 20° C. and washed with THF to yield 120 g (86%) of the title product. (mp: 225°-8° C.) (C23H25N3O3.HCl).

Example 2

N-<1-(2phenylethyl-4-piperidinyl>-3(2H)oxo-1,2-benzoisothiazol-2-acetamide 1,1-dioxide, hydrochloride A solution of 7.7 g of 1-(2-phenylethyl)-piperidinamine in 150 ml of dry THF is added over a slurry of 10 g of 3(2H)oxo-1,2-benzoisothiazol-2-acetic acid 1,1-dioxide and 8.5 g of DCC in 150 ml of dry THF. The heterogeneous mixture is stirred at room temperature for 24 h, then filtered and the filtrate concentrated in vacuo to dryness. The residue is crystallized from HCl-saturated EtOH to afford the title compound in 70–75% yield. (12–13 g).

(mp: 25° C., (d)) ($C_{22}H_{25}N_3O_4S \cdot HCl$).

We claim:

1. A compound of structural formula I:

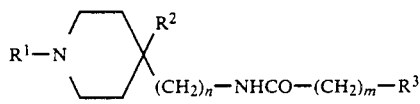

wherein the substituent $R^1$ represents a phenyl-alkylene grouping Ar—$CH_2$ or Ar—$CH_2$—$CH_2$, in which Ar is a benzene ring substituted by from one to two of the substituents selected from the group consisting of:

F, Cl, Br, I, $CH_3$, $C_2H_5$, OH, $OCH_3$, $OCOCH_3$, $CF_3$, $NH_2$, $NHCOCH_3$, $NHSO_2CH_3$, $NO_2$ and COOH, n=0, 1 or 2, m=1 or 2, $R^2$ is H or OH, $R^3$ represents an isoindole ring-system, selected from the group consisting of 1H-2-isoindolyl-1,3(2H)-dioxo, 1H-2-(isoindolyl-1,3(2H)-dioxo-4,4a,5,6,7,7a-hexahydro, 1H-2-isoindolyl-1,3(2H)-dioxo-4,4a,7,7a-tetrahydro, 1H-2-isoindolyl-1,3(2H)-dioxo-4-nitro, and 1H-2-isoindolyl-1,3(2H)-dioxo-4-nitro, and 1H-2-isoindolyl-1,3(2H)-dioxo-4-amino or a pharmacologically acceptable salt thereof.

2. A compound according to claim 1, wherein the substituent $R^1$ is phenylmethyl or 2-phenylethyl, n=0, m=1, and $R^2$ is H.

3. A compound according to claim 1, wherein the substituent $R^1$ is phenylmethyl or 2-phenylethyl, n=0, m=2, and $R^2$ is H.

4. A compound according to claim 1, wherein the substituent $R^1$ is phenylmethyl or 2-phenylethyl, n=1, m=1, and $R^2$ is H or OH.

5. A compound according to claim 1, wherein the substituent $R^1$ is phenylmethyl or 2-phenylethyl, n=1, m=2, and $R^2$ is H or OH.

6. A compound according to claim 1, wherein the substituent $R^1$ is phenylmethyl, n=2, m=1, and $R^2$ is H.

7. A compound according to claim 1, wherein the substituent $R^1$ is phenylmethyl or 2-phenylethyl, n=2, and $R^2$ is H.

8. A compound according to claim 1 in the form of a pharmacologically acceptable salt, said salt being selected from the group consisting of the hydrochloride, hydrobromide, maleate, tartrate, citrate and ethanedioate salt of said compound.

* * * * *